(12) United States Patent
Goren et al.

(10) Patent No.: US 10,238,593 B2
(45) Date of Patent: Mar. 26, 2019

(54) SYSTEM AND METHOD FOR PREVENTING ALOPECIA

(71) Applicant: FOLLEA INTERNATIONAL, Irvine, CA (US)

(72) Inventors: Ofer A. Goren, Irvine, CA (US); John McCoy, Irvine, CA (US)

(73) Assignee: Follea International, Irvine, CA (US)

( * ) Notice: Subject to any disclaimer, the term of this patent is extended or adjusted under 35 U.S.C. 154(b) by 0 days.

(21) Appl. No.: 15/524,012

(22) PCT Filed: Nov. 13, 2015

(86) PCT No.: PCT/US2015/060663
§ 371 (c)(1),
(2) Date: May 3, 2017

(87) PCT Pub. No.: WO2016/077744
PCT Pub. Date: May 19, 2016

(65) Prior Publication Data
US 2017/0333316 A1 Nov. 23, 2017

Related U.S. Application Data

(60) Provisional application No. 62/080,137, filed on Nov. 14, 2014, provisional application No. 62/099,830, filed on Jan. 5, 2015, provisional application No. 62/213,355, filed on Sep. 2, 2015, provisional application No. 62/221,863, filed on Sep. 22, 2015.

(51) Int. Cl.
| | | |
|---|---|---|
| *A61K 8/41* | (2006.01) | |
| *A61K 31/137* | (2006.01) | |
| *A61K 9/00* | (2006.01) | |
| *A61K 31/4174* | (2006.01) | |
| *A61K 36/752* | (2006.01) | |
| *A61Q 7/00* | (2006.01) | |
| *A61K 9/08* | (2006.01) | |
| *A61K 8/9789* | (2017.01) | |

(52) U.S. Cl.
CPC .............. *A61K 8/41* (2013.01); *A61K 8/9789* (2017.08); *A61K 9/0014* (2013.01); *A61K 9/08* (2013.01); *A61K 31/137* (2013.01); *A61K 31/4174* (2013.01); *A61K 36/752* (2013.01); *A61Q 7/00* (2013.01)

(58) Field of Classification Search
USPC ........................................................ 514/740
See application file for complete search history.

(56) References Cited

U.S. PATENT DOCUMENTS

| | | |
|---|---|---|
| 4,034,109 A | 7/1977 | Rowsell et al. |
| 4,853,216 A * | 8/1989 | Koslo .................... A61K 8/41 424/73 |
| 5,055,456 A | 10/1991 | Harris et al. |
| 5,750,141 A | 5/1998 | Roberts et al. |
| 5,922,341 A | 7/1999 | Smith et al. |
| 6,294,517 B1 | 9/2001 | Garvey et al. |
| 6,747,008 B1 | 6/2004 | Rodgers et al. |
| 8,114,898 B2 * | 2/2012 | Shanler ................ A61K 31/00 514/227.2 |
| 2004/0198706 A1 | 10/2004 | Carrara et al. |
| 2006/0110415 A1 | 5/2006 | Gupta |
| 2006/0252734 A1 | 11/2006 | Woodward |
| 2007/0287733 A1 | 12/2007 | Snorrason |
| 2008/0011314 A1 | 1/2008 | Arroyo et al. |
| 2009/0068287 A1 | 3/2009 | Welsh et al. |
| 2009/0306026 A1 | 12/2009 | Tuiten et al. |
| 2012/0316246 A1 | 12/2012 | Fahl et al. |
| 2013/0199348 A1 | 8/2013 | Aberizk |
| 2014/0011774 A1 | 1/2014 | Dalton et al. |
| 2017/0135988 A1 | 5/2017 | Goren et al. |
| 2017/0165253 A1 | 6/2017 | Goren et al. |
| 2017/0333316 A1 | 11/2017 | Goren et al. |
| 2018/0078499 A1 | 3/2018 | Goren et al. |

FOREIGN PATENT DOCUMENTS

| | | |
|---|---|---|
| WO | 97/04764 A1 | 2/1997 |
| WO | 2004/041259 A1 | 5/2004 |
| WO | 2010/123184 A1 | 10/2010 |
| WO | 2016/077744 A1 | 5/2016 |

OTHER PUBLICATIONS

International Search Report (PCT/ISA/210) dated Jan. 28, 2016, by the U.S. Patent Office as the International Searching Authority for International Application No. PCT/US2015/060663.
Written Opinion (PCT/ISA/237) dated Jan. 28, 2016, by the U.S. Patent Office as the International Searching Authority for International Application No. PCT/US2015/060663.
Hellmann, "The isolated pilomotor muscles as an in vitro preparation", J Physiol, 1963, pp. 603-620, 169.
Siepmann et al., "Quantitative pilomotor axon reflex test: a novel test of pilomotor function", Arch Neurol, 2012, pp. 1488-1492, 69(11).
Lewis et al., "Observations upon a pilomotor reaction in response to faradism", J Physiol, 1927, pp. 87-106, 64(1).
Piascik et al., "Alpha1-adrenergic receptors: new insights and directions", J Pharmacol Exp Ther, 2001, pp. 403-410, 298(2).
Wyness et al., "Trichotillometry: the reliability and practicality of hair pluckability as a method of nutritional assessment", Nutr J, 2007, pp. 1-6.
Smelser et al., "Field use of hair epilation force in nutrition status assessment", Am J Clin Nutr. 1982, pp. 342-346, 35.
Moftah et al., "Glutathione Peroxidase and Malondialdehyde in Skin Lesions of Acne Vulgaris", Journal of the Egyptian Women's Dermatologic Society, 2011, pp. 25-29, 8.

(Continued)

*Primary Examiner* — Rei Tsang Shiao
(74) *Attorney, Agent, or Firm* — Buchanan Ingersoll & Rooney PC

(57) ABSTRACT

Traction alopecia and other disorders related to mechanical pulling on hair are treated or prevented by administering a topical composition comprising an alpha-1 adrenergic receptor agonist or another compound or electrical stimulation to contract the arrector pili muscle.

24 Claims, 5 Drawing Sheets

(56) References Cited

OTHER PUBLICATIONS

Allahdadi et al., "Female Sexual Dysfunction: Therapeutic Options and Experimental Challenges," Cardiovasc Hematol Agents Med Chem., (Oct. 2009), vol. 7, No. 4, pp. 260-269.
Coon et al., "The Nature of the Pilomotor Response to Acetylcholine; Some Observations on the Pharmacodynamics of the Skin," The journal of Pharmacology and Experimental Therapeutics, (1939), vol. 68, Issue 3, pp. 301-311.
Dave et al., "Transpapillary Drug Delivery to the Breast," PLoS ONE, (Dec. 29, 2014), vol. 9, No. 12, pp. 1-16.
Eglen et al., "Muscarinic Acetylcholine receptor Subtypes in Smooth Muscle," Trends in Pharmacological Sciences, (Apr. 1994), vol. 15, Issue 4, pp. 114-119.
Galitovskiy et al., "Muscle Sarcomas and Alopecia in A/J Mice Chronically Treated with Nicotine," Life Sciences, (Nov. 27, 2012), vol. 91, No. 21-22, pp. 1109-1112.
Harrison et al., "Self-Reports of Nipple Erection in Emotional and Somatic Contexts," The Psychological Record, (Jul. 2013), vol. 63, pp. 1-12.
Heatherton et al., "Development and Validation of a Scale for Measuring State Self-Esteem," Journal or Personality and Social Psychology, (1991), vol. 60, No. 6, pp. 895-910.
Karlsson et al., "Snake Toxins with High Selectivity for Subtypes of Muscarinic Acetylcholine Receptors," Biochimie, (Sep.-Oct. 2000), vol. 82, No. 9-10, pp. 793-806.
Levin, "The Breast/Nipple/Areola Complex and Human Sexuality," Sexual and Relationship Therapy, (2006), vol. 21, Issue 2, pp. 237-249. (Abstract Only).
Levin et al., "Nipple/Breast Stimulation and Sexual Arousal in Young Men and Women," The Journal of Sexual Medicine, (May 2006), vol. 3, Issue 3, pp. 450-454. (Abstract Only).
Moser, "Comparisons of the Acute Effects of Cholinesterase Inhibitors Using a Neurobehavioral Screening Battery in Rats," Neurotoxicology and Teratology, (Nov.-Dec. 1995), vol. 17, Issue 6, pp. 617-625.
Rosenberg, "Rosenberg's Self-Esteem Scale," Society and the adolescent self-image, Princeton University Press, Princeton NJ (1965), accessed at www.wwnorton.com/college/psych/psychsci/media/rosenberg.htm on Mar. 13, 2017.
Rothman et al., "Axon Reflex Responses to Acetyl Choline in the Skin," The Journal of Investigative Dermatology, (1940) vol. 3, pp. 79-97.
Santos et al., "Drug Discovery for Alopecia: Gone Today, Hair Tomorrow," Expert Opinion on Drug Discovery, (2015), vol. 10, No. 3, pp. 269-292.
Schlenz et al., "Mastopexy and Breast Reduction," Shiffman, M.A., Ed., Springer-Verlag, Berlin, 2009, Chapter 79, pp. 618-619.
Siepmann et al., "The Quantitative Pilomotor Axon-Reflex Test (QPART)—A Technique to Assess Autonomic Nerve Fiber Function (Po5.197)," Neurology (Apr. 25, 2012), vol. 78, No. 1 Supplement Po5.197. (Abstract Only).
Stein et al., "Nipple Stimulation for Labor Augmentation," The Journal of Reproductive Medicine, (Jul. 1990), vol. 35, No. 7, pp. 710-714. (Abstract Only).
Wright et al., "Female Sexual Dysfunction," Medical Clinics of North America, (May 2015), vol. 99, Issue 3, pp. 607-628. (Abstract Only).
Non-final Office Action issued in co-pending U.S. Appl. No. 15/354,743, 107 pages (dated Oct. 19, 2017).
International Search Report issued in International Patent Application No. PCT/US2016/062576, 3 pages (dated Jan. 24, 2017).
Written Opinion issued in International Patent Application No. PCT/US2016/062576, 5 pages (dated Jan. 24, 2017).
Extended European Search Report for EP 15858397.1 dated Jul. 17, 2018.
Final Office Action for U.S. Appl. No. 15/354,743 dated Jul. 20, 2018.
Non-Final Office Action for U.S. Appl. No. 15/524,012 dated Dec. 1, 2017.
Final Office Action for U.S. Appl. No. 15/524,012 dated Apr. 20, 2018.

\* cited by examiner

| PATIENT # | GRAMS OF FORCE [AVG (STD)] | | INCREASE |
|---|---|---|---|
| | EXPERIMENTAL | CONTROL | |
| 5 | 14.6 (4.8) | 2.6 (1.5) | 462% |
| 1 | 13.0 (6.6) | 2.6 (2.6) | 400% |
| 4 | 26.0 (7.9) | 6.8 (6.4) | 282% |
| 10 | 30.2 (8.3) | 9.4 (4.8) | 221% |
| 3 | 34.8 (2.9) | 15.2 (2.4) | 129% |
| 9 | 22.0 (5.5) | 11.2 (5.9) | 96% |
| 2 | 24.8 (2.9) | 16.6 (2.7) | 49% |
| 8 | 20.4 (4.6) | 14.6 (4.2) | 40% |
| 6 | 23.6 (11.1) | 18.0 (3.2) | 31% |
| 7 | 18.4 (2.3) | 17.6 (4.4) | 5% |

EPILATORY FORCE THRESHOLD ON SCALP HAIR FOLLICLES FOLLOWING TOPICAL PE APPLICATION INCREASED BY APPROXIMATELY 172%

FIG. 4

SYSTEM AND METHOD FOR PREVENTING ALOPECIA

FIELD

The present invention is directed to methods for treating, reducing or preventing alopecia and other hair loss disorders caused by mechanical pulling of the hair, including but not necessarily limited to traction alopecia, and compositions, devices and kits useful in such methods.

BACKGROUND

Traction alopecia results from the chronic application of tensile force to scalp hair (1). The condition was described as early as 1907 in subjects from Greenland who had developed hair loss due to prolonged wearing of tight ponytails (2). Traditionally, the term "traction alopecia" has been related to specific hairstyles that cause increased tension on the scalp (e.g., ponytails, Afro-Caribbean hair styles with tight braiding or the tightly wound turbans of Sikh men). It has also been seen in female ballerinas. It is also seen in cultural traditions where the hair is voluntarily not cut in religious obeisance, which causes progressively increasing weight of the hair itself. Traction alopecia is mechanical in etiology, rather than androgenic. Management includes cessation of the chronic traction. However, this is unacceptable to people who favor the specific hairstyles and styling techniques that give rise to the condition.

Traction alopecia is a substantial risk in hair extensions and weaves, which can be worn either to conceal hair loss, or purely for cosmetic purposes. The latter involves creating a braid around the head below the existing hairline, to which an extended-wear hairpiece, or wig, is attached. Because the hair of the braid is still growing, it requires frequent maintenance, which involves the hairpiece being removed, the natural hair braided again, and the piece snugly reattached. The tight braiding and snug hairpiece cause tension on the hair that is already at risk for falling out. Traction alopecia is one of the most common causes of hair loss in African American women. "Traction alopecia" includes hair loss or shedding due to increased traumatic force on hair follicles caused by hairstyle or mechanical hair procedures such as blow drying, flat ironing, hair curling and chronic brushing. Traction alopecia can also develop in patients constantly pulling their hair such as in trichotillomania.

In traction alopecia, affected areas depend on the etiology of the disorder, but usually hair loss is localized on frontal and temporal scalp. According to population studies in African women, prevalence of traction alopecia varies from 17.1% in young women (6-21 years) to 31.7% in older women (18-86 years). Clinical features of traction alopecia include itching of the scalp, perifollicular erythema, scaling, folliculitis, and pustules, but it can also present as slow onset of hair loss without other symptoms. Primarily, traction alopecia is considered noncicatricial, yet excessive tension can lead to permanent alopecia, due to physical damage of hair follicles. Prolonged force on hair follicles may lead to inflammatory changes in immune cell infiltrate and fibrosis can result. Therefore, it is important to recognize the condition early, while it is still reversible.

In view of the popularity of hairstyles that result in traction alopecia, and the desirability of use of hairstyling and care products that may cause traction alopecia, there is a need for treatment and prevention of hair loss associated with the condition.

SUMMARY

Compositions and methods are disclosed herein for the treatment and prevention of hair loss disorders caused at least in part by repeated application of tensile force to hair, including, without limitation, traction alopecia. Such disorders may be treated or prevented by the application to the hair follicle or scalp of a compound or agent that induces contraction of the arrector pili (AP) muscle, such as, without limitation, alpha 1 adrenergic receptor agonists (A1AR agonists).

BRIEF DESCRIPTION OF THE DRAWINGS

The accompanying drawings exemplify embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIGS. 4 and 5 depict epilatory force thresholds on scalp hair follicles following topical phenylephrine application according to the procedures described in example 3.

DETAILED DESCRIPTION

Figure 1B:
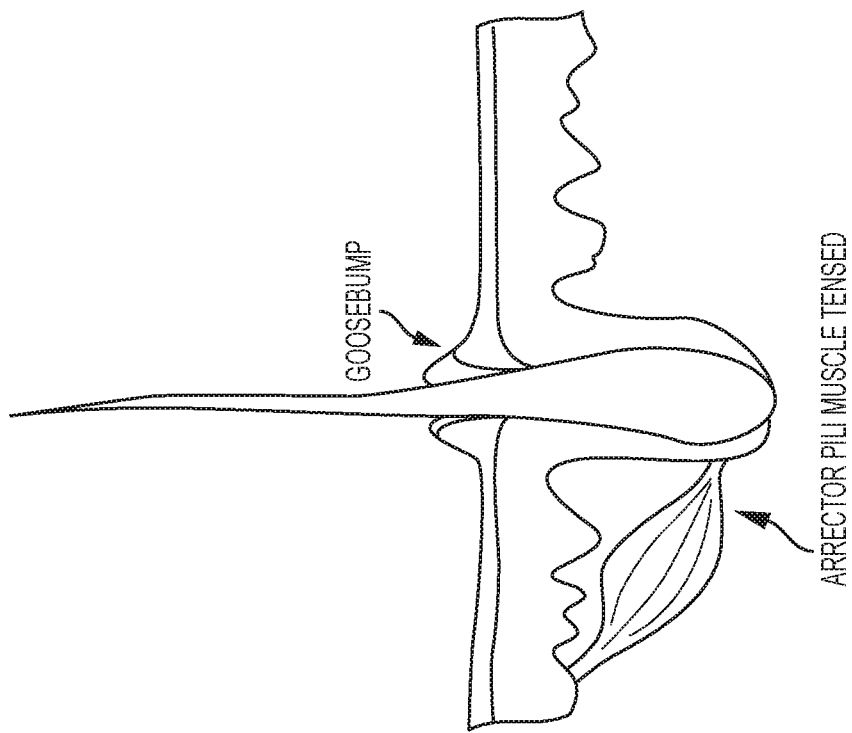
FIG. 1B depicts a cross sectional view of the hair follicle and the arrector pili muscle in a tensed state.

Each hair follicle in the scalp contains an arrector pili muscle that, when contracted, erects the hair. The smooth muscle in the arrector pili expresses α1 adrenergic receptors ("A1AR"). Disclosed herein are methods for the treatment and prevention of disorders associated with mechanical stress or pulling on the hair comprising topical administration to the scalp or hair follicle of a composition comprising one or more A1AR agonists. As shown herein, such agonists protect against hair loss or shedding as shown by an increase in epilation force needed to remove a hair and reduction in the number of hairs removed after brushing. Without intending to be limited or bound by theory, Applicants postulate that contraction of the arrector pili muscle via an A1AR agonist increases the threshold of force required to pluck hair during cosmetic procedures and while under mechanical stress. Thus, it is believed that the compounds and agents used in the present invention stimulate contraction of the AP muscle and thereby reduce hair loss by increasing the force required to remove the hair.

The use of A1AR agonists to promote the pilomotor effect is described in U.S. Pat. No. 4,853,216, which is incorporated herein by reference in its entirety. There, the A1AR agonists were recognized as useful for causing hairs to stand up to facilitate closer shaving or to potentiate the effect of depilatories. That is, A1AR agonists were described there as agents that facilitate hair removal, as opposed to prevent hair loss.

While the disclosure most often specifically refers to A1AR agonists as agents useful for treating and preventing the disorders described herein relating to hair loss, it should be understood that any agent that stimulates contraction of smooth muscle, and particularly the AP muscle, can be useful in the compositions and methods described herein.

That is, unless specifically indicated otherwise, disclosure relating to uses or formulations of A1AR agonists should be considered to refer as well to other agents that stimulate AP muscle contraction.

As used herein, the term "traction alopecia" means a form of alopecia (hair loss or hair shedding) associated with mechanical forces that pull the hair such as hair brushing hair combing, flat ironing, wearing of extensions, hair braiding, and ponytail style hair. Under this definition, although chronic traction on the hair can lead to traction alopecia, the mechanical forces that pull the hair do not necessarily need to be chronic to lead to hair loss or excessive shedding.

As used herein, the term "pilomotor effective" refers to an agent or treatment that stimulates contraction of the arrector pili muscle associated with a hair follicle. A "pilomotor effective amount" of an agent or treatment is an amount sufficient to stimulate contraction of the arrector pili muscle.

As used herein, the term "alpha 1 adrenergic receptor agonist" refers to a ligand that binds the alpha 1 adrenergic receptor on smooth muscle cells and activates smooth muscle contraction.

As used herein, the terms "prevent" or "prevention" and other derivatives of the words, when used in reference to alopecia, e.g., traction alopecia, refer to a reduced likelihood of alopecia in an individual receiving a given treatment relative to that of a similar individual at risk for alopecia but not receiving that treatment. As such, the terms "prevent" and "prevention" encompass a treatment that results in a lesser degree of alopecia, e.g., traction alopecia, than would be otherwise expected for a given individual. Efficacy for prevention of alopecia, e.g., traction alopecia, can be established through controlled studies, e.g., in which a subject is administered a treatment (e.g., a topical treatment) at one site likely to experience or exhibit alopecia (e.g., for traction alopecia, a site at which hair is pulled for an extended period of time) but not at another site subjected to the same conditions. Under these circumstances, if the site treated with the topical treatment undergoes less hair loss over time relative to the untreated site, e.g., at least 5% less, at least 10% less, at least 15% less, at least 20% less, at least 25% less, at least 30% less, at least 35% less, at least 40% less, at least 45% less, at least 50% less or beyond, the treatment is effective for the prevention of alopecia, e.g., traction alopecia. Efficacy for the prevention of other forms of alopecia can be established in a similar manner, e.g., by treating one area affected by or likely to be affected by such alopecia, but not another, substantially similar area (i.e., subject to the same conditions causing alopecia or a likelihood of alopecia) and comparing hair loss or retention in the two areas.

As used herein, the terms "treat," "treatment," or "treating" refer to therapeutic treatments, wherein the object is to reverse, alleviate, ameliorate, inhibit, slow down or stop the progression or severity of a disease or condition, e.g., traction alopecia or other form of alopecia. The term "treating" includes reducing or alleviating at least one adverse effect or symptom of a disease or condition, e.g., traction alopecia or other form of alopecia. Treatment is generally "effective" if one or more symptoms are reduced. Alternatively, treatment is "effective" if the progression of a disease is reduced or halted. That is, "treatment" includes not just the improvement of symptoms, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the extent or amount of hair loss is reduced, or the progression of hair loss is slowed or halted. The term "treatment" of a disease also includes providing relief from the symptoms or side-effects of the disease (including palliative treatment).

As used herein, the term "epilatory" relates to the removal of hair. As used herein, the term "increasing epilatory force" refers to any treatment that increases the physical force required to remove a hair. As noted, the increase in force can be viewed as at least a partial balancing of a traction force by the force exerted by the arrector pili muscle—the vector direction of the arrector pili muscle's force of contraction need not necessarily be directly opposed to a traction force on the hair shaft to increase the epilatory force required to remove the hair, but the net effect is that the muscle provides at least a partial counter-acting force to the traction force, whether it directly pulls back on the hair or simply holds the hair or hair follicle more tightly in place. An increase in epilatory force can be measured in several ways, including empirically, through a reduction in traction alopecia (e.g., 10% or less reduction in hair loss) despite continued or ongoing traction, or through measurement of actual force exerted on the hair follicle, e.g., with a myograph, trichotilometer, or a device used to measure tensile forces.

As used herein the term "comprising" or "comprises" is used in reference to compositions, methods, etc. refers to component(s) or method steps that are present in the method or composition, yet allows for the composition, method, etc. to also include unspecified elements.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In various aspects, the technology described herein relates to the prevention of traction alopecia. One preventive approach currently available for traction alopecia is to remove, limit or avoid the application of a traction force to the hair. Thus, hairstyles or other factors that pull on the hair (e.g., tight fitting helmets) should normally be avoided to prevent traction alopecia. However, by using the approaches set out herein, such as the application of an A1AR agonist to the hair follicle or scalp, one can limit, reduce or prevent as that term is defined herein the traction alopecia-inducing effects of such hairstyles or factors despite the ongoing traction involved. This preventive approach permits one to wear a hairstyle, helmet, etc., that would normally have a high risk of inducing traction alopecia without actually suffering the traction-related hair loss.

Various aspects of the technology described herein involve pilomotor stimulation. The measurement or detection of pilomotor stimulation can be performed, at its simplest, by observation of the area at the base of the hair shaft—an agent or treatment that induces arrector pili contraction causes the hair follicle to "stand up" and causes puckering of the skin around the hair shaft commonly referred to as "goose bumps." Thus, if an agent is applied and the hair stands up, goose bumps form, or both, the agent has stimulated the arrector pili. Measurement of the strength of arrector pili muscle contraction can be performed, if necessary, via myograph adapted for that purpose. Examples are described in, e.g., Zeveke & Gladysheva, Bull. Exp. Biol. Med. 71: 102-105 (1971); Hellmann, J. Physiol. 169: 603-620 (1963); Wyness L A, McNeill G, Prescott G L. Trichotillometry: the reliability and practicality of hair pluckability as a method of nutritional assessment. Nutr J 2007: 6: 9; and Chase E S, Weinsier R L, Laven G T, Krumdieck C L. Trichotillometry: the quantitation of hair pluckability as a method of nutritional assessment. Am J Clin Nutr 1981: 34(10): 2280-2286. each of which is incorporated herein in its entirety by reference. Other systems to measure the strength of the arrector pili muscle can use a trichotillometer or a device used to measure tensile forces. Traction alopecia is a form of alopecia, or gradual hair loss, caused primarily by pulling force applied to the hair. Several different hair styles and hair extensions can cause or exacerbate traction alopecia. For example, certain styles or braiding patterns that pull the hairline have been shown to cause traction alopecia. Particularly tight braids, barrettes, or the installation of hair extensions can exert sufficient chronic force on the hair follicles to cause traction alopecia. Generally, traction alopecia has a mechanical origin based on the force on the hair. For example, chronic pulling on the hair follicles can cause inflammation. Eventually, follicular scarring and permanent alopecia can occur from prolonged pulling.

Figure 1A:
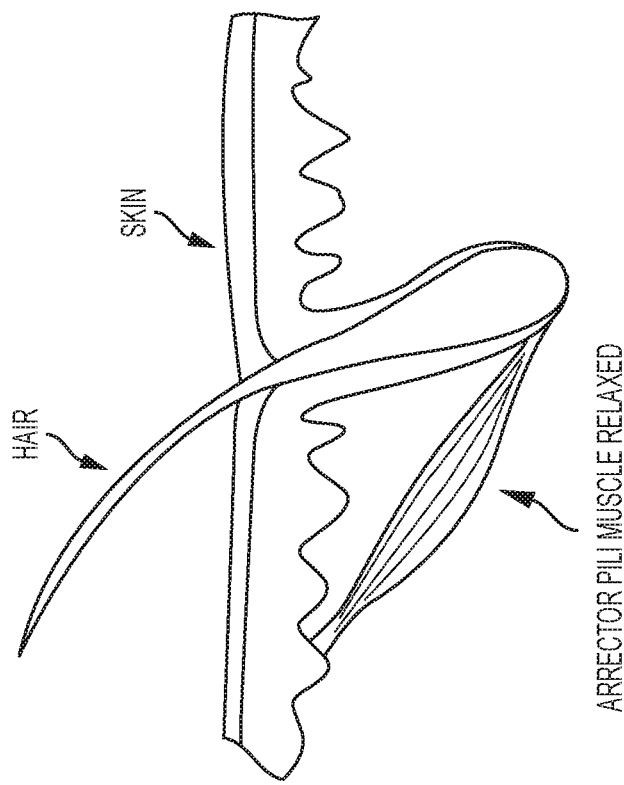
FIG. 1A depicts a cross sectional view of the hair follicle and the arrector pili muscle in a relaxed state.

Accordingly, the mechanical strain of the pulling force on the root causes the damage to the follicle in the root. Additionally, as illustrated in FIGS. 1A-1B, each follicular unit contains a smooth muscle anchoring the hair to the epidermis. When the smooth muscle is relaxed as illustrated in FIG. 1A, the muscle does not supply much restraining force and the follicle can be removed easily. When the smooth muscle or arrector pili (AP) contracts as illustrated in FIG. 1B, the follicle stands up and is restrained by additional force from the smooth muscle rather than just primarily the surrounding connective tissue of the dermis. Accordingly, the smooth muscle can provide more retention force in opposition to a force that would pull on the hair to dislodge the follicle if it is contracted. Thus, by contracting the arrector pili (AP) muscle, the root can be more firmly grounded into the dermis of the skin preventing the mechanical strain from damaging the root and dermis, i.e. requiring a larger epilation force for removal of the hair follicle. This would prevent the chronic stressing from pulling of the hair observed in different hairstyles from doing as much damage to the root, and thereby would prevent or reduce the risk of developing traction alopecia.

In some aspects, then, the technology described herein relates to the reduction of the force exerted on the root of a hair. In practice, this "reduction" in force is more akin to providing a better balancing force against a traction on the hair itself—that is, the treatments described herein will not necessarily reduce the amount of traction on the hair, but by stimulating the contraction of the arrector pili muscles, the treatments provide a force that at least partially counters the effect of the traction or pulling force, thereby protecting the root against the epilatory effect of the traction.

Accordingly, disclosed herein are methods for contracting the smooth muscle cells or arrector pili while a patient is wearing a hair extension, wig, a tightly woven or pulling hairstyle, combing their hair, or engaging in other behavior that pulls back on the follicles of the hair. Several methods are disclosed for contracting the AP muscle including application of a pharmaceutical composition containing an A1AR agonist, electrical stimulation of the hair follicles and others.

Disorders to be Treated or Prevented

Applicants disclose herein methods to treat or prevent various conditions related to mechanical stress on the human hair. In one embodiment, the invention concerns treating, reducing or preventing hair loss from disorders such as traction alopecia, androgenic alopecia (also known as androgenetic alopecia), alopecia areata, and alopecia universalis, and hair loss due to hair brushing, combing, etc. comprising topical administration to a person in need thereof of a therapeutically effective amount of an A1AR agonist. In another embodiment, the invention concerns a method for the reduction of the force exerted on a root of a hair comprising topical administration to a person in need thereof of a therapeutically effective amount of an A1AR agonist. In another embodiment, the invention concerns a method for increasing hair epilation force comprising topical administration to a person in need thereof of a therapeutically effective amount of an A1AR agonist. In another embodiment, the invention concerns a cosmetic method for piloerecting hair or raising hair comprising topical administration to a person in need thereof of a therapeutically effective amount of an A1AR agonist.

In one aspect, the therapeutically effective amount of the agent administered, such as the A1AR agonist, is a pilomotor effective amount. In one aspect, the therapeutic agent, such as the A1AR agonist, is applied to a skin section, such as a section of the scalp, that contains at least one hair follicle. In a further embodiment, the at least one hair follicle is under tension.

A1AR agonists may be administered to the hair follicle or scalp to promote contraction of the AP muscle and thereby reduce, treat or prevent alopecia and the other disorders discussed herein. It is specifically contemplated that an A1AR agonist or any other agonist of smooth muscle contraction known in the art or disclosed herein can be administered to the hair follicle or the scalp in combination with an agent that retards systemic absorption of the agent across the dermis. In this manner, agents that might otherwise have unwanted systemic effects can be used to treat, reduce or prevent alopecia or other disorders discussed herein while avoiding such systemic side effects. One formulation of agents for topical administration in a manner that avoids systemic absorption is discussed in detail in U.S. 2009/0068287, which is incorporated herein by reference in its entirety.

In another aspect, described herein is a method for prevention of traction alopecia comprising: applying a therapeutically effective amount, such as a pilomotor effective amount, of an A1AR agonist to the scalp to an area with a group of follicles that will experience a pulling force from a hair augmentation device; and attaching the hair augmentation device to the group of follicles. In one embodiment, the hair augmentation device is a hair extension or extensions. In another embodiment the hair augmentation device is a weave. In another embodiment, the hair augmentation device is a barrette.

In another aspect, described herein is method of reducing hair shedding, such as occurs during brushing, combing, weaving, flat ironing, showering, curling, wift, attaching hair extensions or wigs, trading, pony tails, or cosmetic procedures, the method comprising applying a therapeutically effective amount, such as a pilomotor effective amount, of an A1AR agonist topically to a portion of skin that includes at least one hair follicle. In one embodiment, the A1AR agonist is present on a brush or comb that may then be used to administer the therapeutic agent such as the A1AR agonist. In another embodiment, the A1AR agonist is applied to the skin prior to the brushing or combing.

In another aspect, the cosmetic procedure is selected from the group consisting of brushing, braiding, flat ironing, and combinations of two or more thereof. The therapeutic agent, such as the A1AR agonist, may be topically applied once, twice, or more often per day. In another embodiment, the A1AR agonist is applied to the skin twice daily. In another embodiment, the A1AR agonist is applied to the skin prior to the cosmetic procedure.

In another aspect, described herein is a method for treatment of trichotillomania comprising applying a pilomotor effective amount of an A1AR agonist topically to a portion of skin that includes at least one hair follicle.

The disclosure also concerns evaluating an individual for susceptibility to treatment according to the methods disclosed herein. In one embodiment, the method comprises (1) applying an A1AR agonist (e.g., without limitation, synephrine) on a site on the skin of a person; and (2) 30 to 60 minutes after applying, observe whether the person's skin shows goosebumps or pilioerection at the site; wherein if pilioerection or goosebumps are observed, diagnosing the person as likely to be a successful candidate for use of the alpha 1 adrenergic receptor agonist for any of the many methods of treatment or prevention described herein. This method may be combined with any of the other methods of treatment or prevention or reduction of hair loss described herein to provide an initial diagnosis of those people most likely to benefit from the methods described. The step of application to the skin may be, in one embodiment, applying a bandage or patch coated with the alpha 1 adrenergic receptor agonist to the person's arm or thigh. In another embodiment of any composition or method involving an A1AR agonist, the agonist is synephrine or phenylephrine.

Formulations

The therapeutic agents, particularly the A1AR agonists, described herein and used in the present methods may be formulated into compositions according to the knowledge of one of skill in the art. In one embodiment, the A1AR agonist or other stimulator of AP muscle contraction is formulated for topical slow or prolonged release. As but one example, in one embodiment the AP stimulating agent is encapsulated for slow release and integrated into a hair extension.

In another embodiment, the A1AR agonist or other stimulator of AP muscle contraction is formulated in a shampoo (which can reduce hair shedding during hair brushing), a foam, ointment, spray, solution, gel, slow release capsule, oral tablet, or any similar compound or delivery vehicle or methodology. Topical application is preferred. In one embodiment, the composition is formulated in a topical cream. In another embodiment, the composition is formulated in a hair styling product selected from the group consisting of a styling gel, a styling foam, and a hair conditioner.

In another embodiment, the composition may comprise an exfoliating agent to promote abrasion of the surface of the scalp. Examples of the exfoliating agent include (1) inorganic and/or metallic particles such as: boron nitride, in body-centered cubic form (Borazon®); aluminosilicate (e.g. nepheline); zircon; mixed oxides of aluminum such as emery; zinc oxide; aluminum oxides such as aluminas or corundum; titanium oxide; titanium oxide coated mica; carbides, in particular silicon carbide (carborundum); or other metal oxides; metals, and metal alloys such as iron shot, steel shot, and in particular perlite; silicates such as glass, quartz, sand, or vermiculite; calcium carbonate (e.g. Bora-Bora sand or Rose de Brignoles sand) or magnesium carbonate; sodium chloride; pumice stone; amorphous silica; diamond; ceramics, and (2) organic particles such as: fruit stones, in particular apricot stones, e.g. Scrubami® apricot; wood cellulose, e.g. ground bamboo stem; coconut shell, e.g. coconut exfoliator; polyamides, in particular Nylon-6; sugars; plastic microbeads, e.g. polyethylenes or polypropylenes; ground walnut; ground apricot seed; ground shells, and (3) mixed particles associating organic and inorganic compounds, and particles coated in the above compounds. The exfoliating agents may be in the form of microbeads of less than five millimeters in its largest dimension that have an exfoliating effect.

In one embodiment, the composition comprising an A1AR agonist can be formulated as a drug. In one embodiment, the composition comprising an A1AR agonist can be formulated as a cosmetic product.

In another embodiment, the AP muscle can be contracted via electrical stimulation to the scalp. The stimulation can be controlled by a battery and control unit embedded into a hair extension, or in, e.g., a hair brush or comb. The control unit can contain an accelerometer to detect the optimal time to contract the AP muscles based on the posture of the subject or the subject's hair.

The amount of therapeutic agent present in the composition may be determined by one of skill in the art using known methodologies. In certain embodiments, the A1AR agonist or other stimulator of AP muscle contraction is present in the composition in a concentration from about 0.20% to 0.30%, or about 0.25% by weight. In another embodiment, the therapeutic agent such as an A1AR agonist is present in the composition in a concentration of about 0.25%, 0.33%, 0.5%, 1%, 2%, 2.5%, or 10% by weight.

In other embodiments, the therapeutic agent, such as the A1AR agonist, is present in the topical composition for use in the methods disclosed herein in a concentration from about 0.1% to 35%, about 1.0% to 30%, about 0.2% to 30%, about 0.2% to 25%, about 0.2% to 20%, about 0.2% to 15%, about 0.2% to 10%, about 0.2% to 5%, about 0.2% to 4%, about 0.2% to 3%, about 0.2% to 2%, about 0.2% to 1%, about 10.0% to 30%, about 15.0% to 30%, about 20.0% to 30%, about 10% to 20%, about 10% to 15%, about 15% to 20%, about 15% to 60%, about 20% to 60%, about 50% to 60%, and about 45% to 55% by weight. For certain therapeutic agents, such as synephrine (racemic mixture), a concentration of about 25% to 60%, 30% to 50%, 30% to 60%, 25% to 30%, 40% to 50%, or 50% to 55% by weight of the total weight of the composition is desirable.

In one embodiment, the composition comprises an A1AR agonist in a concentration of about 0.25%, about 0.33%, about 0.5%, about 1%, about 2%, about 2.5%, about 3.0%, about 4.0%, about 10%, about 15%, about 20%, or about 25% by weight.

The compositions used in the present disclosure, particularly compositions containing an A1AR agonist, may be formulated with a preservative such as EDTA (0.1-0.5% by weight of the formulation) and/or sodium metabisulfite (0.1-0.5% by weight of the formulation). In some embodiments, the composition includes a penetration enhancer, such as a penetration enhancer selected from one or more of the group consisting of alcohols, glycols, fatty acids, fatty esters, fatty ethers, occlusive agents, surface active agents, dimethylaminopropionic acid derivatives, terpenes, sulfoxides, cyclic ethers, amides, and amines. Other components of the formulations used herein may be chosen from cosmetically approved excipients known in the art, including water, thickeners, etc.

The composition may be packaged in a kit with an applicator for application to the skin. The invention is also directed to a kit comprising a composition of the therapeutic agent, such as an A1AR agonist, and an applicator, and to a kit comprising a composition of the therapeutic agent, such as an A1AR agonist, and a hair brush or comb, particularly a brush or comb that provides exfoliating effect on the scalp such that there is light abrasion after its use that enhances penetration of the therapeutic agent to the AP muscle. In one embodiment, the therapeutic agent is provided in a metered dose applicator that provides for a fixed volume of the composition to be administered with each administration, such as 1 ml of the topical composition per administration.

It will be understood that the ranges described above, and throughout this document, are also intended to encompass single values contained within these ranges. For example, for a formulation comprising a particular ingredient in a range between 1-50%, a percentage of 5% or 49% is also intended to be disclosed.

Therapeutic Agents

The methods of the present disclosure may be used with an A1AR agonist or other compound that causes contraction directly or indirectly of the AP muscle. Suitable A1AR agonists can be utilized including phenylephrine, cirazoline, desvenlafaxine, etilfrine, metaraminol, methoxamine, naphazoline, oxymetazoline, pseudoephrine, m-synephrine, p-synephrine, synephrine, octopamine, hordenine, tetrahydrozoline, isometheptene, metaraminol, nicergoline, ergonovine, levonordefrin, phendimetrazine, methoxamine, midodrine, clonidine, pergolide, xylometazoline, droxidopa, epinephrine, mephentermine, 4-methoxyamphetamine, Benzphetamine, Naphazoline, Apraclondine, Bromocriptine, Oxymetazoline, Phenylpropanolamine, Pseudoephedrine, Dipivefrin, xylometazoline, and *citrus aurantium* (e.g. bitter orange extract). Additionally, derivatives of A1AR agonists can be utilized including derivatives of the compounds mentioned above. In other embodiments, a prodrug that is activated to become an A1AR agonist can be utilized. For example, midodrine is one such prodrug. A particular prodrug can be activated by endogenous enzymes in the scalp such as Caspase-1 when follicular inflammation is present, e.g., at the location of application of a hair extension. In one embodiment, the A1AR agonist is synephrine. In one embodiment, the A1ARA is phenylephrine or synephrine, including compositions comprising the 1-enantiomer of synephrine, which is R-(−)-4-[1-hydroxy-2-(methylamino)ethyl]phenol, that are essentially free of other enantiomers of synephrine, or in which less than 30%, 25%, 20%, 15%, 10%, 12%, 5%, 3%, 1%, or 0.5% by weight of the synephrine present in the composition is a different enantiomer. The synephrine enantiomer R-(−)-4-[1-hydroxy-2-(methylamino)ethyl]phenol may be obtained from natural bitter orange extract. In one embodiment, the therapeutic agent is derived from bitter orange, *Citrus aurantium*, or is an extract of bitter orange, such as a bitter orange extract that contains 95%, 96%, 97%, 98%, 90%, 80%, 70%, 60%, 50%, 40%, 30%, 20%, 10%, 9%, 8%, 7%, 6%, 5%, 4%, 3%, or 2% by weight or from 5-10%, 10-15%, 5-15%, 20-25%, 15-20%, 25-30%, 30-35%, 35-40%, 40-45%, 45-55%, 50-60%, 60-70%, 70-80%, 80-90%, 85-95%, or 90-99% of one enantiomer of synephrine, R-(−)-4-[1-hydroxy-2-(methylamino)ethyl]phenol. Extracts of bitter orange contain high levels of only one synephrine enantiomer, namely, R-(−)-4-[1-hydroxy-2-(methylamino)ethyl]phenol, and are preferred for use in the present methods and compositions of the disclosure. In one embodiment, the compositions of the present invention contain 10%, 11%, 12%, 13%, 14%, 15%, 16%, 17%, 18%, 19%, 20%, 21%, 22%, 23%, 24%, 25%, 16%, 27%, 28%, 29%, 30% or 31% by weight of bitter orange extract, such as an extract that contains 3-5%, 5-10%, 6%, 9%, 10-15%, 15-20%, 20-40%, 40-60%, 60-80%, or 80-95% synephrine, or the composition contains from about 5-10%, 10-15%, 15-20%, 25-30% or 30-40% by weight of bitter orange extract, such as an extract containing from about 3-5%, 5-10%, 6%, 9%, 10-15%, 15-20%, 20-30%, 30-50%, 50-60%, 60-70%, 70-80%, 80-90% or 80-99% synephrine. In a preferred embodiment, the compositions of the present invention contain 10%, 11%, 12%, 13%, 14%, 15%, 16%, 17%, 18%, 19%, 20%, 21%, 22%, 23%, 24%, 25%, 16%, 27%, 28%, 29%, 30% or 31% by weight of a bitter orange extract, wherein the extract contains 50-90%, 50-60%, 60-70%, 70-80%, 80-90%, 85-95% or 90-99% synephrine and substantially all of the synephrine in the extract is the enantiomer R-(−)-4-[1-hydroxy-2-(methylamino)ethyl]phenol.

In one embodiment, the A1AR agonist is phenylephrine, or a pharmaceutically acceptable salt or hydrate thereof, in a composition in a concentration of 0.25% to 40%, 0.25% to 25% by weight, or 0.5% to 22.5% by weight, or 0.75% to 20% by weight, or 1% to 17.5% by weight, or 1.5% to 15% by weight, or 2% to 14.5% by weight, or 2.5% to 14% by weight, or 5% to 13.5% by weight, or 7.5% to 12.5% by weight, or 8% to 12% by weight, or 8.5% to 11.5% by weight, or 9% to 11% by weight, or 9.25% to 10.75% by weight, or 9.5% to 10.5% by weight, or 9.6% to 10.4% by weight, or 9.7% to 10.3% by weight, or 9.8% to 10.2% by weight, or 9.9% to 10.1% by weight, or 9.95% to 10.05% by weight, or 9.96% to 10.04% by weight, or 9.97% to 10.03% by weight, or 9.98% to 10.02% by weight, or 9.99% to 10.01% by weight.

In one embodiment, the A1AR agonist is phenylephrine, or a pharmaceutically acceptable salt or hydrate thereof, in a composition in a concentration at a range of 0.25%, 0.5%, 0.75%, 1%, 1.5%, 2%, 2.5%, 5%, 7.5%, 8%, 8.5%, 9%, 9.25%, 9.5%, 9.6%, 9.7%, 9.8%, 9.9%, 9.95%, 9.96%, 9.97%, 9.98%, or 9.99% by weight as the lower weight limit of the range to an upper weight limit of 10.01%, 10.02%, 10.03%, 10.04%, 10.05%, 10.1%, 10.2%, 10.3%, 10.4%, 10.5%, 10.75%, 11%, 11.5%, 12%, 12.5%, 13.5%, 14%, 14.5%, 15%, 17.5%, 20%, 22.5%, 25%, 30%, 35%, 40%, 45%, or 50% by weight (e.g., a range of 0.25% to 10.01%, 0.25% to 10.02%, 0.5% to 10.01%, 0.5% to 10.02%, etc.).

In one embodiment, the A1AR agonist is phenylephrine, or a pharmaceutically acceptable salt or hydrate thereof, in a composition in a concentration of 0.25% by weight, or 0.5% by weight, or 0.75% by weight, or 1% by weight, or 1.5% by weight, or 2% by weight, or 2.5% by weight, or 5% by weight, or 7.5% by weight, or 8% by weight, or 8.5% by weight, or 9% by weight, or 9.25% by weight, or 9.5% by weight, or 9.6% by weight, or 9.7% by weight, or 9.8% by weight, or 9.9% by weight, or 9.95% by weight, or 9.96% by weight, or 9.97% by weight, or 9.98% by weight, or 9.99% by weight, or 10% by weight, or 10.01% by weight, or 10.02% by weight, or 10.03% by weight, or 10.04% by weight, or 10.05% by weight, or 10.1% by weight, or 10.2% by weight, or 10.3% by weight, or 10.4% by weight, or 10.5% by weight, or 10.75% by weight, or 11% by weight, or 11.5% by weight, or 12% by weight, or 12.5% by weight, or 13.5% by weight, or 14% by weight, or 14.5% by weight, or 15% by weight, or 17.5% by weight, or 20% by weight, or 22.5% by weight, or 25% by weight, or 30% by weight, or 40% by weight, or 45% by weight, or 50% by weight, or 55% by weight.

In another embodiment, the composition comprises an A1AR agonist that is synephrine, or a pharmaceutically acceptable salt or hydrate thereof, or that comprises one enantiomer of synephrine, namely R-(−)-4-[1-hydroxy-2-(methylamino)ethyl]phenol and is substantially free of other enantiomer(s) of synephrine or has less than 30%, 25%, 20%, 15%, 10%, 12%, 5%, 3%, 1%, or 0.5% by weight of the synephrine present in the composition as a different enantiomer, wherein the synephrine is present in the composition in a concentration of 30% to 70% by weight, or 35% to 65% by weight, or 37.5% to 62.5% by weight, or 40% to 60% by weight, or 42.5% to 57.5% by weight, or 45% to 55% by weight, or 45.5% to 54.5% by weight, or 46% to 54% by weight, or 46.5% to 53.5% by weight, or 47% to 53% by weight, or 47.5% to 52.5% by weight, or 48% to 52% by weight, or 48.25% to 51.75% by weight, or 48.5% to 51.5% by weight, or 48.75% to 51.25% by weight, or 49% to 51% by weight, or 49.25% to 50.75% by weight, or 49.5% to 50.5% by weight, or 49.6% to 50.4% by weight, or 49.7% to 50.3% by weight, or 49.8% to 50.2% by weight, or 49.9% to 50.1% by weight.

In another embodiment, the composition comprises an A1AR agonist that is synephrine, or a pharmaceutically acceptable salt or hydrate thereof, or that comprises one enantiomer of synephrine, namely R-(−)-4-[1-hydroxy-2-(methylamino)ethyl]phenol and is substantially free of other enantiomer(s) of synephrine or has less than 30%, 25%, 20%, 15%, 10%, 12%, 5%, 3%, 1%, or 0.5% by weight of the synephrine present in the composition as a different enantiomer, wherein the synephrine is present in the composition in a concentration of 20% by weight, or 25% by weight, or 30% by weight, or 35% by weight, or 37.5% by weight, or 40% by weight, or 42.5% by weight, or 45% by weight, or 45.5% by weight, or 46% by weight, or 46.5% by weight, or 47% by weight, or 47.5% by weight, or 48% by weight, or 48.25% by weight, or 48.5% by weight, or 48.75% by weight, or 49% by weight, or 49.25% by weight, or 49.5% by weight, or 49.6% by weight, or 49.7% by weight, or 49.8% by weight, or 49.9% by weight to 50.1% by weight, or 50.2% by weight, or 50.3% by weight, or 50.4% by weight, or 50.5% by weight, or 50.75% by weight, or 51% by weight, or 51.25% by weight, or 51.5% by weight, or 51.75% by weight, or 52% by weight, or 52.5% by weight, or 53% by weight, or 53.5% by weight, or 54% by weight, or 54.5% by weight, or 55% by weight, or 57.5% by weight, or 60% by weight, or 62.5% by weight, or 65% by weight, or 70% by weight.

In one embodiment, the composition comprises an A1AR agonist that is R-(−)-4-[1-hydroxy-2-(methylamino)ethyl]phenol substantially free of the other enantiomer of synephrine (or having less than 25%, 20%, 15%, 10%, 5%, 1% or 0.1% of the other enantiomer of synephrine) or a pharmaceutically acceptable salt or hydrate thereof, in a composition in a concentration of 20% by weight, or 21% by weight, or 25% by weight, or 26% by weight, or 30% by weight, or 35% by weight, or 37.5% by weight, or 40% by weight, or 42.5% by weight, or 45% by weight, or 45.5% by weight, or 46% by weight, or 46.5% by weight, or 47% by weight, or 47.5% by weight, or 48% by weight, or 48.25% by weight, or 48.5% by weight, or 48.75% by weight, or 49% by weight, or 49.25% by weight, or 49.5% by weight, or 49.6% by weight, or 49.7% by weight, or 49.8% by weight, or 49.9% by weight, or 50% by weight, or 50.1% by weight, or 50.2% by weight, or 50.3% by weight, or 50.4% by weight, or 50.5% by weight, or 50.75% by weight, or 51% by weight, or 51.25% by weight, or 51.5% by weight, or 51.75% by weight, or 52% by weight, or 52.5% by weight, or 53% by weight, or 53.5% by weight, or 54% by weight, or 54.5% by weight, or 55% by weight, or 57.5% by weight, or 60% by weight, or 62.5% by weight, or 65% by weight, or 70% by weight.

In another embodiment, the composition comprises an A1AR agonist that is synephrine, or a pharmaceutically acceptable salt or hydrate thereof, or that comprises one enantiomer of synephrine, namely R-(−)-4-[1-hydroxy-2-(methylamino)ethyl]phenol and is substantially free of other enantiomer(s) of synephrine or has less than 30%, 25%, 20%, 15%, 10%, 12%, 5%, 3%, 1%, or 0.5% by weight of the synephrine present in the composition as a different enantiomer, wherein the synephrine is present in the composition in a concentration of 10% to 60% by weight, or 12.5% to 50% by weight, or 10% to 50% by weight, or 15% to 40% by weight, or 20% to 30% by weight, or 20% to 40% by weight, or 17.5% to 30% by weight, or 20% to 25% by weight, or 20.5% to 24.5% by weight, or 21% to 24% by weight, or 21.5% to 23.5% by weight, or 21.75% to 23.25% by weight, or 22% to 23% by weight, or 22.1% to 22.9% by weight, or 22.2% to 22.8% by weight, or 22.3% to 22.7% by weight, or 22.4% to 22.6% by weight.

In another embodiment, the composition comprises an A1AR agonist that is synephrine, or a pharmaceutically acceptable salt or hydrate thereof, or that comprises one enantiomer of synephrine, namely R-(−)-4-[1-hydroxy-2-(methylamino)ethyl]phenol and is substantially free of other enantiomer(s) of synephrine or has less than 30%, 25%, 20%, 15%, 10%, 12%, 5%, 3%, 1%, or 0.5% by weight of the synephrine present in the composition as a different enantiomer, wherein the synephrine is present in the composition in a concentration of 10% by weight, or 12.5% by weight, or 15% by weight, or 17.5% by weight, or 20% by weight, or 20.5% by weight, or 21% by weight, or 21.5% by weight, or 21.75% by weight, or 22% by weight, or 22.1% by weight, or 22.2% by weight, or 22.3% by weight, or 22.4% by weight to 22.6% by weight, or 22.7% by weight, or 22.8% by weight, or 22.9% by weight, or 23% by weight, or 23.25% by weight, or 23.5% by weight, or 24% by weight, or 24.5% by weight, or 25% by weight, or 30% by weight, or 40% by weight, or 50% by weight, or 60% by weight.

In one embodiment, the composition comprises one enantiomer of synephrine, namely R-(−)-4-[1-hydroxy-2-(methylamino)ethyl]phenol, and is substantially free of other enantiomer(s) of synephrine or has less than 30%, 25%, 20%, 15%, 10%, 12%, 5%, 3%, 1%, or 0.5% by weight of the synephrine present in the composition as a different enantiomer, wherein the R-(−)-4-[1-hydroxy-2-(methylamino)ethyl]phenol is present in the composition in a concentration of 20% to 25% by weight.

In a further embodiment, the A1AR agonist is oxymetazoline, or a pharmaceutically acceptable salt or hydrate thereof, in a composition in a concentration of 0.01% to 2% by weight, or 0.02% to 1.75% by weight, or 0.03% to 1.5% by weight, or 0.04% to 1.25% by weight, or 0.05% to 1% by weight, or 0.1% to 0.9% by weight, or 0.15% to 0.85% by weight, or 0.2% to 0.8% by weight, or 0.25% to 0.75% by weight, or 0.3% to 0.7% by weight, or 0.35% to 0.65% by weight, or 0.4% to 0.6% by weight, or 0.41% to 0.59% by weight, or 0.42% to 0.58% by weight, or 0.43% to 0.57% by weight, or 0.44% to 0.56% by weight, or 0.45% to 0.55% by weight, or 0.46% to 0.54% by weight, or 0.47% to 0.53% by weight, or 0.48% to 0.52% by weight, or 0.49% to 0.51% by weight.

In a further embodiment, the A1AR agonist is oxymetazoline, or a pharmaceutically acceptable salt or hydrate thereof, in a composition in a concentration of 0.01% by weight, or 0.02% by weight, or 0.03% by weight, or 0.04% by weight, or 0.05% by weight, or 0.1% by weight, or 0.15% by weight, or 0.2% by weight, or 0.25% by weight, or 0.3% by weight, or 0.35% by weight, or 0.4% by weight, or 0.41% by weight, or 0.42% by weight, or 0.43% by weight, or 0.44% by weight, or 0.45% by weight, or 0.46% by weight, or 0.47% by weight, or 0.48% by weight, or 0.49% by weight to 0.51% by weight, or 0.52% by weight, or 0.53% by weight, or 0.54% by weight, or 0.55% by weight, or 0.56% by weight, or 0.57% by weight, or 0.58% by weight, or 0.59% by weight, or 0.6% by weight, or 0.65% by weight, or 0.7% by weight, or 0.75% by weight, or 0.8% by weight, or 0.85% by weight, or 0.9% by weight, or 1% by weight, or 1.25% by weight, or 1.5% by weight, or 1.75% by weight, or 2% by weight.

In a further embodiment, the A1ARA is oxymetazoline, or a pharmaceutically acceptable salt or hydrate thereof, in a composition in a concentration of 0.01% by weight, or 0.02% by weight, or 0.03% by weight, or 0.04% by weight, or 0.05% by weight, or 0.1% by weight, or 0.15% by weight, or 0.2% by weight, or 0.25% by weight, or 0.3% by weight, or 0.35% by weight, or 0.4% by weight, or 0.41% by weight, or 0.42% by weight, or 0.43% by weight, or 0.44% by weight, or 0.45% by weight, or 0.46% by weight, or 0.47% by weight, or 0.48% by weight, or 0.49% by weight, or 0.5% by weight, or 0.51% by weight, or 0.52% by weight, or 0.53% by weight, or 0.54% by weight, or 0.55% by weight, or 0.56% by weight, or 0.57% by weight, or 0.58% by weight, or 0.59% by weight, or 0.6% by weight, or 0.65% by weight, or 0.7% by weight, or 0.75% by weight, or 0.8% by weight, or 0.85% by weight, or 0.9% by weight, or 1% by weight, or 1.25% by weight, or 1.5% by weight, or 1.75% by weight, or 2% by weight.

In some embodiments, provided herein is an A1AR agonist formulated with a carrier or delivery vehicle optimized for delivery of the A1AR agonist to the scalp. An A1AR agonist can be released using several different formulations or release methods including time release, creams, ointments, sprays, capsules, or other release methods. For instance the A1AR agonist can be incorporated into a shampoo for utilization during showering so that when a user brushes their hair, their follicles will be tightly held by the AP muscles to prevent brushing from unnecessarily pulling out healthy hair. In other embodiments, the A1AR agonist can be included in ointments or other topical creams that could be applied to the scalp so that it can be slowly absorbed into the skin and stimulate the smooth muscle. In other embodiments, the A1AR agonist can be included in a liquid spray or aerosol medium to be applied to the scalp. In other embodiments, the A1AR agonist can be incorporated into capsules or other slow release vehicles that would allow the chemical or agent to be slowly released into the dermis of the scalp. Capsules or vehicles that encapsulate the A1AR agonist can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the scalp. It is specifically contemplated that the A1AR agonist can be formulated in hair care products such as styling gel, styling foam, hair conditioner, hair serum, a hair mask, etc.

Any of the aforementioned A1AR agonist can be applied by a user before the application of a hair extension device or other device or condition that exerts force on the hair follicle. Alternatively, an A1AR agonist can be used routinely (e.g. twice daily) after such a device has been installed. Routine use of an A1AR agonist would be indicated as a prophylactic against traction alopecia for users of a hair extension device or other device that exerts force on the hair follicle.

Creams or other formulations with different A1AR agonists can be applied prior to a user utilizing a hair piece or brushing the hair. In some embodiments, a hair piece or hair extensions can contain pads or other absorbent material that can absorb A1AR agonist in a foam or cream applied prior to application to a user's head. In other embodiments, slow release capsules can be incorporated into the hair extensions or hair pieces, or can be included in barrettes. In some embodiments, barrettes will include pads with an absorbent layer for application of A1AR agonist cream or other A1AR agonist topical formulation.

Efficacy of treatment to treat or prevent traction alopecia can be determined by monitoring the density of hairs on a given area of the subject's body, e.g., a given area of the scalp. If the rate of hair loss is reduced, e.g., by 10% or more following treatment, the treatment is effective for the prevention of traction alopecia. Similarly, if hair density remains the same, despite ongoing traction that would normally have been expected to cause traction alopecia, the treatment is effective for the prevention of traction alopecia. If the density of hair increases, e.g., by 5% or more, e.g., by 10% or more following treatment and despite ongoing traction, the treatment is also considered effective for the treatment and/or prevention of traction alopecia.

As noted above, it is contemplated that all forms of alopecia can benefit from the technology described herein. For example, the technology described herein can be applicable to prevent or treat androgenic alopecia. The AP muscle degenerates in the process of androgenic alopecia (reviewed, e.g., in Torkamani et al., Int. J. Trichology 6:88-94 (2014)); without wishing to be bound by theory, it is contemplated that regular stimulation of AP muscle contraction may slow or reduce the loss of the muscle and thereby benefit the treatment or prevention of androgenic alopecia.

It is also contemplated that the technology described herein can be broadly applicable to any type of condition of which at least one hair follicle is under tension. Using the A1AR agonist compositions or other agents that stimulate AP muscle contraction as described herein, it is contemplated that one can limit or reduce hair shedding under such conditions.

In one aspect, the condition of which at least one hair follicle is under tension is brushing or combing. Accordingly, the technology described herein relates to a method of reducing hair shedding during brushing or combing. As used herein, the term "reducing hair shedding" means that the amount of hair shedding from a subject is reduced by at least 5%, at least 10%, at least 15%, at least 20%, at least 25%, at least 30%, at least 35%, at least 40%, at least 45%, at least 50%, or more, as compared to what would be expected in the absence of the method. An A1AR agonist or other agent that stimulates AP muscle contraction can be present on the brush or comb used for the brushing or combing. In one embodiment, the A1AR agonist or other agent can be applied to the brush or comb prior to brushing or combing, e.g., in the form of a liquid, gel, cream or spray. In one embodiment, the brush or comb can dispense the A1ARA or other agent.

Agents that promote the contraction of the AP muscle can optionally be administered by iontophoresis, which uses an electric field to drive the passage of ionic agents or drugs into the skin. As but one example, iontophoresis has been used to deliver agents such as phenylephrine to the skin to stimulate AP muscle contraction (See, e.g., Siepmann et al., Neurology Apr. 25, 2012; 78 (Meeting Abstracts 1): P05.197). Thus, in one embodiment, a brush or comb can incorporate an iontophoresis device, which can dispense the A1ARA or other agent and/or be used for transdermal delivery of the agent(s). The iontophoresis device can comprise one or more metal contacts. Optionally, the iontophoresis device can comprise one or more compartments for containing the A1AR agonist or other agent(s).

In another aspect, the condition in which at least one hair follicle is under tension is a hair-related cosmetic procedure. Accordingly, the technology described herein relates to a method of reducing hair shedding during a hair-related cosmetic procedure. Examples of hair-related cosmetic procedures include, but are not limited to, brushing, braiding, flat ironing, and combinations thereof.

In another aspect, the condition in which at least one hair follicle is under tension is trichotillomania, a disorder characterized by the compulsive urge to pull out one's hair. Accordingly, to the extent that increasing the force required to remove the hair can help counter hair loss due to this condition, the stimulation of AP muscle contraction as described herein can provide a method to reduce the hair loss.

Electrical Stimulation

In another embodiment of the invention, the AP muscle can be contracted via electrical stimulation to the scalp or dermis of the skull. The electrical stimulation can be controlled, e.g., by a unit contained in a brush or a comb, or, e.g., embedded in a hair extension. In some embodiments, the control unit can contain an accelerometer to detect the optimal time to contract the AP muscles based on the posture of the subject or the subject's hair. In some embodiments, a strain or other force gauge attached to a portion of a hair extension can test the force pulling on the patient's hair. Then, the electrical stimulator could vary the amount of current, voltage or other component of the electrical stimulation applied to vary the strength of smooth muscle contraction based on the amount of force pulling on the hair at a certain time. In other embodiments, the control unit can deliver a standard amount of current to the hair in order to reach the electrical threshold for contraction of the AP muscle. This can advantageously minimize the amount of current being applied to the scalp overall and the amount of electricity. Accordingly, one advantage of utilizing electrical stimulation to contract the muscle, is that the strength of the contraction can be varied accordingly.

Examples of applying electrical forces to contract the AP muscles are described in, for example, US Patent Publication US2013/0199348 published on Aug. 8, 2013, titled Pilomotor Effect Stimulating Device and Method, which is incorporated by reference herein in its entirety. For example, in some embodiments, the voltage or amplitude of the signal applied to the scalp can be in the range of 35 to 75 volts, 25 to 50 volts, 10-30 volts or other suitable ranges to reach the threshold for muscle contraction. The current applied to a scalp by a device as disclosed herein can, in some embodiments, preferably be in the microamps to avoid electrocution of the user. A frequency of 10 KHz to 15 KHz can be applied, or a lower or higher frequency. In some embodiments, the pulse length applied will be from 1 to 50 milliseconds, 1 to 100 milliseconds, or other suitable lengths to contract the AP muscle or any other pilomotor effective amount of current. In some embodiments, a control unit will automatically pulse the electrical stimulation at random intervals that are enough to keep the AP muscle relatively contracted. In other embodiments, the pulses will be spaced out enough to allow the AP muscle to relax in between pulses.

The disclosure also concerns a device for hair augmentation and prevention of traction alopecia comprising: a hair augmentation device; and an electrical stimulation device connected to the hair augmentation device, the electrical stimulation device comprising: a battery; a memory; an electrical stimulation generator; a scalp probe in electrical communication with the electrical stimulation generator for applying an electrical stimulus; and a controller in communication with the battery, memory, and electrical stimulation and memory wherein the controller commands the electrical stimulus generator to output a pilomotor effective amount of electrical stimulus. In certain embodiments, the pilomotor effective amount of electrical stimulus is between 10-100 volts, or between 10-15 kHz. In some embodiments the pilomotor effective amount of electrical stimulus is applied for 1 to 100 milliseconds. In some embodiments, the pilomotor effective amount of electrical stimulus is applied periodically with rest periods long enough to allow the AP muscle to relax between stimuli. In other embodiments, the pilomotor effective amount of electrical stimulus is applied periodically with rest periods short enough to prevent the AP muscle from relaxing between stimuli. The hair augmentation device may be any product that when applied to the hair exerts a pulling force on the hair. For example, the hair augmentation device may be a hair extension, a weave, or a barrette.

In some embodiments, a probe or electrical prongs can be attached to a hair extension or other hair piece that would deliver the charge to the scalp. In some embodiments, the probe can be connected to a control unit with an on switch, a processor, and memory with firmware or other software instructions for delivering the desired pulses. Different control units can contain more advanced circuitry and algorithms for processing accelerometer or force data and varying the electrical stimulus accordingly. In some embodiments, the probe can be connected to any portion of a hair piece using any suitable apparatus and method.

Other Agents or Approaches to Contract the Smooth Muscle

Other agents or approaches can be used to contract the smooth muscle for the prevention or treatment of alopecia, e.g., traction alopecia. As noted above, any agent or treatment that stimulates AP muscle contraction is of potential use in methods of treating, reducing or preventing alopecia as described herein.

In one embodiment, the smooth muscle can be contracted by stimulating or activating a cold receptor. A cold receptor can be stimulated, for example, by activating the TRPM8 channel. Exemplary agents that can stimulate a cold receptor include, but are not limited to, menthol and icilin. Compositions and methods for stimulating a cold receptor are disclosed, for example, in U.S. Pat. No. 4,034,109, the contents of which are incorporated by reference in its entirety.

Where the AP muscle is served by or associated with both noradrenergic fibers and a cholinergic system, agents that stimulate release of transmitters from these systems can be used to stimulate AP muscle contraction. Thus, not only alpha 1 adrenergic agonists, but also cholinergic agonists, including, but not limited to acetylcholine and other neurotransmitters that stimulate smooth muscle contraction are contemplated for use in the methods and compositions described herein.

The alpha 1 adrenergic receptor is a G protein-coupled receptor. Agonists of other G protein-coupled receptors (e.g., alpha 2 adrenergic receptor) can also be used to stimulate contraction of the smooth muscle. Examples of alpha 2 adrenergic receptor agonists include, but are not limited to, 4-NEMD, 7-Me-marsanidine, agmatine, apraclonidine, brimonidine, clonidine, detomidine, dexmedetomidine, fadolmidine, guanabenz, guanfacine, lofexidine, marsanidine, medetomidine, methamphetamine, mivazerol, rilmenidine, romifidine, talipexole, tizanidine, tolonidine, xylazine, and xylometazoline. As noted above, to the extent that it would be disadvantageous to administer these or other agents systemically, they can be administered in a formulation that permits uptake by the AP muscle in the dermis but limits systemic uptake.

In one embodiment, halostachine (also known as N-methylphenylethanolamine) is contemplated for use as a therapeutic agent in the methods and compositions described herein to stimulate smooth muscle contraction.

It should be noted that agonists described herein also encompass their inorganic or organic salts. Representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

It should be noted that combinations of the above methods and agents can be used to promote the contraction of the smooth muscle.

Treatment of Acne

The compositions described herein can also be used for the treatment of acne. It is known that contraction of the AP muscle plays a role in the secretion of the sebum (see Mahfouz et al., J. Egypt worn. Dermatol. Soc. 2005, 2, 25-29). The compositions can be applied in the form of lotion, cream, spray, or wipe. The compositions can be used in combination with benzoyl peroxide or other topical medications for acne treatment.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

EXAMPLES

Example 1: Oxymetazoline HCl at 0.1%, 0.2%, 0.5% by Weight

A study was conducted to assess the dosage of topical oxymetazoline solution required to elicit the pilomotor reflex of the hair arrector-pili muscle. Five subjects participated in the study. Three formulations were used: Formula A: 0.1% topical oxymetazoline hydrochloride solution; Formula B: 0.2% topical oxymetazoline hydrochloride solution; Formula C: 0.5% topical oxymetazoline hydrochloride solution.

The study was conducted over 3 days. On day 1, subjects were instructed to apply Formula A to their arm. On day 2, subjects were instructed to apply Formula B to their arm. On day 3, subjects were instructed to apply Formula C to their arm. 0.1 mL of each formula was applied using a metered dosage dispenser to each arm. Table 1 summarizes the finding from this study.

TABLE 1

Oxymetazoline study

| Subject No. | Formula A | Formula B | Formula C |
|---|---|---|---|
| 1 | NR | NR | R |
| 2 | NR | NR | R |
| 3 | NR | NR | R |
| 4 | NR | NR | R |
| 5 | NR | NR | R |

R = Response, i.e. goose bumps; NR = No response

The 0.5% topical oxymetazoline solution (Formula C) elicited a clinical response in all subjects while the 0.1% and 0.2% formulations (Formula A and B) failed to elicit a response. With the 0.5% topical oxymetazoline solution, response in the contraction of the arrector-pilomotor muscle was obtained approximately within 1 hour and lasted over 8 hours.

Due to the long acting effect of oxymetazoline it may be beneficial to apply once daily, every other day, or as needed prior to mechanical procedures that may exert epilatory forces on hair follicles.

Example 2: Phenylephrine HCl at 5.0%, 7.5%, 10% by Weight

A study was conducted to assess the dosage of topical phenylephrine solution required to elicit the pilomotor reflex of the hair arrecto-pili muscle. Five subjects participated in the study. Three formulations were used: Formula A: 5.0% topical phenylephrine hydrochloride solution; Formula B: 7.5% topical phenylephrine hydrochloride solution; Formula C: 10.0% topical phenylephrine hydrochloride solution.

The study was conducted over 3 days. On day 1, subjects were instructed to apply Formula A to their arm. On day 2, subjects were instructed to apply Formula B to their arm. On day 3, subjects were instructed to apply Formula C to their arm. 0.1 mL of each formula was applied using a metered dosage dispenser to each arm. Table 2 summarizes the finding from this study.

TABLE 2

Phenylephrine study-1

| Subject No. | Formula A | Formula B | Formula C |
|---|---|---|---|
| 1 | NR | NR | R |
| 2 | NR | NR | R |
| 3 | NR | NR | R |
| 4 | NR | NR | R |
| 5 | NR | NR | R |

R = Response, i.e. goose bumps; NR = No response

The 10.0% topical phenylephrine solution (Formula C) elicited a clinical response in all subjects while the 5.0% and 7.5% formulations (Formula A and B) failed to elicit a response. With the 10.0% topical phenylephrine solution, response in the contraction of the arrector-pilomotor muscle was obtained approximately within 20-30 minutes and lasted over 3 hours.

Due to the shorter lasting acting effect of phenylephrine compared to oxymetazoline it may be beneficial to apply as needed prior to mechanical procedures that may exert epilatory forces on hair follicles.

Example 3: Phenylephrine HCl at 10% by Weight

In another study, 10.0% phenylephrine hydrochloride to assess the use of topical phenylephrine hydrochloride solution as a novel drug for prevention/reduction of hair loss from mechanical pulling. Participants included in the study were female subjects between ages of 18 and 60 who frequently use traumatic hair care practices, such as tight braids, head scarves, ponytails, extensions, hair rollers, hair weaves and heated styling appliances such as blow dryers, flat irons, heat setters and curling irons. Excluded subjects were those who experienced uncontrolled hypertension, those who were pregnant or breastfeeding, those who were diagnosed with pattern hair loss, or those who experienced other hair loss in conjunction with female pattern hair loss. Overall, fifteen female subjects, aged 24 to 40 years, participated in the study.

The study was conducted over 4 days. On day 1, subjects were instructed to wash their hair. On day 2, subjects were instructed to apply 1 mL of placebo solution containing vehicle and brush targeted area after 30 minutes. Brushing was conducted to frontal hair with regular brush in size of 8×10 cm. On day 3, subjects were instructed again to wash their hair. On day 4, subjects were instructed to apply 1 mL of 10% phenylephrine hydrochloride solution on targeted area and brush after 30 minutes. FIGS. 2-5 summarize the finding from this study.

Figure 2:
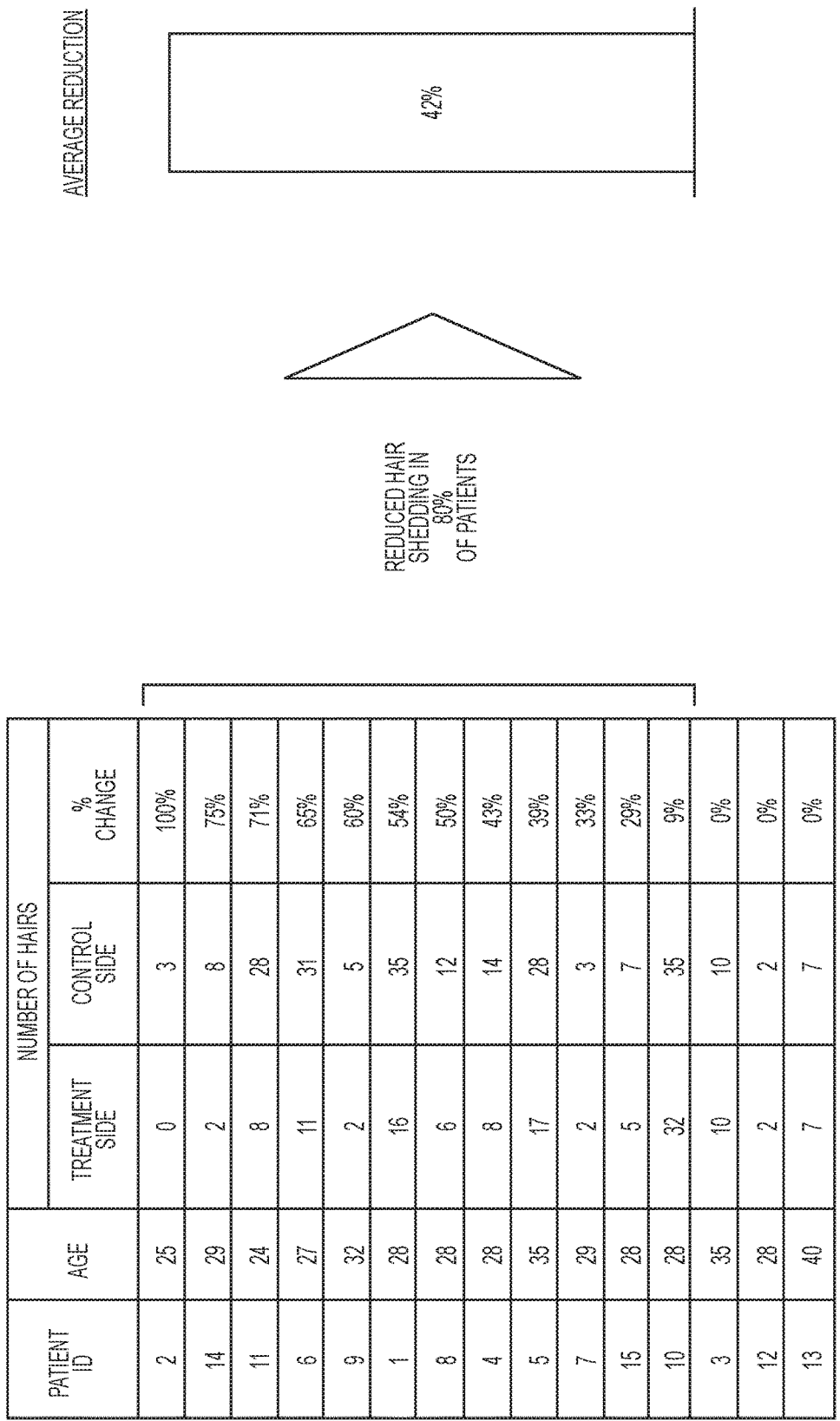
FIGS. 2 and 3 depict hair loss from mechanical pulling according to the experiment reported in example 3.
Figure 3:
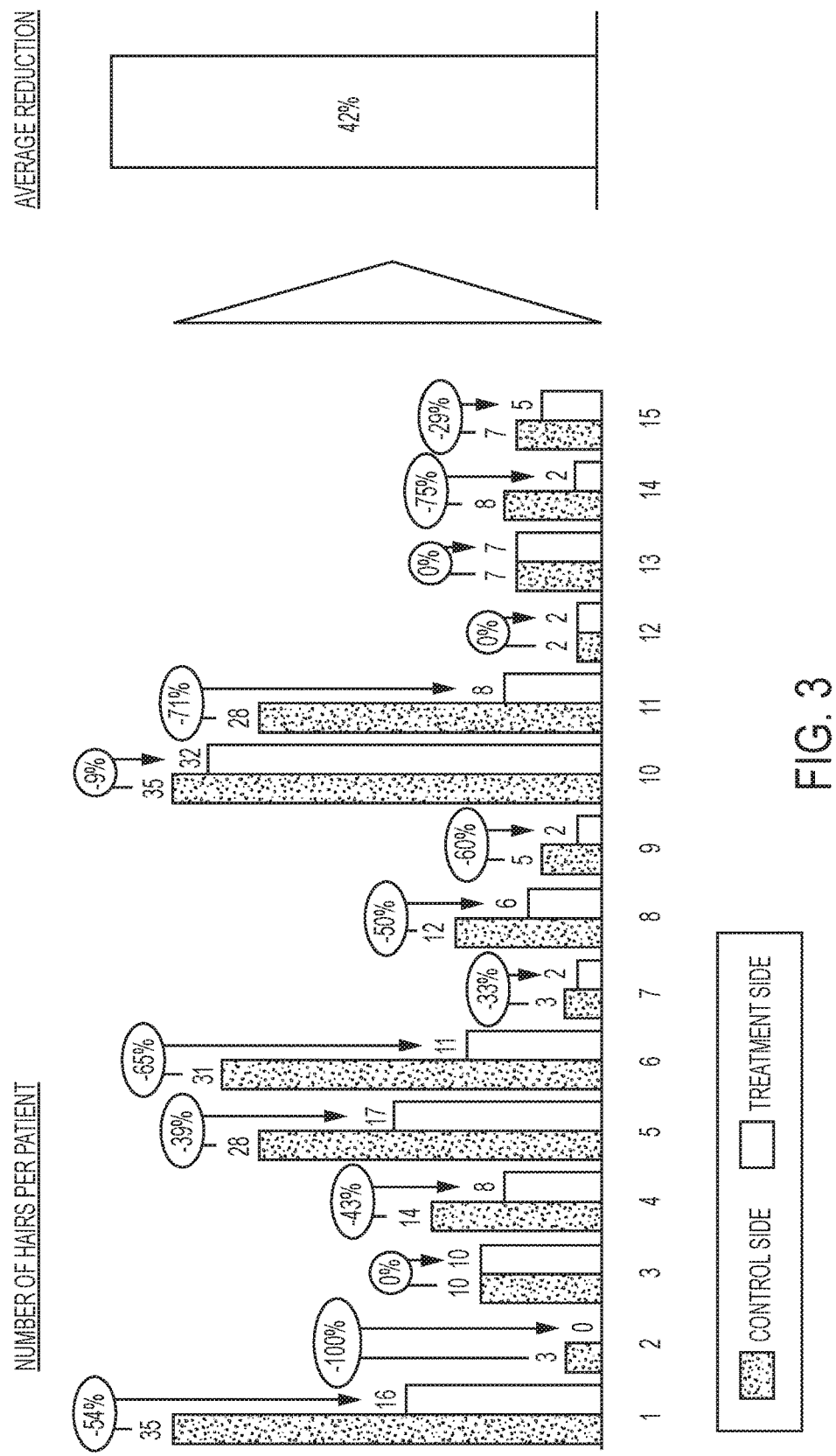
Figure 5:
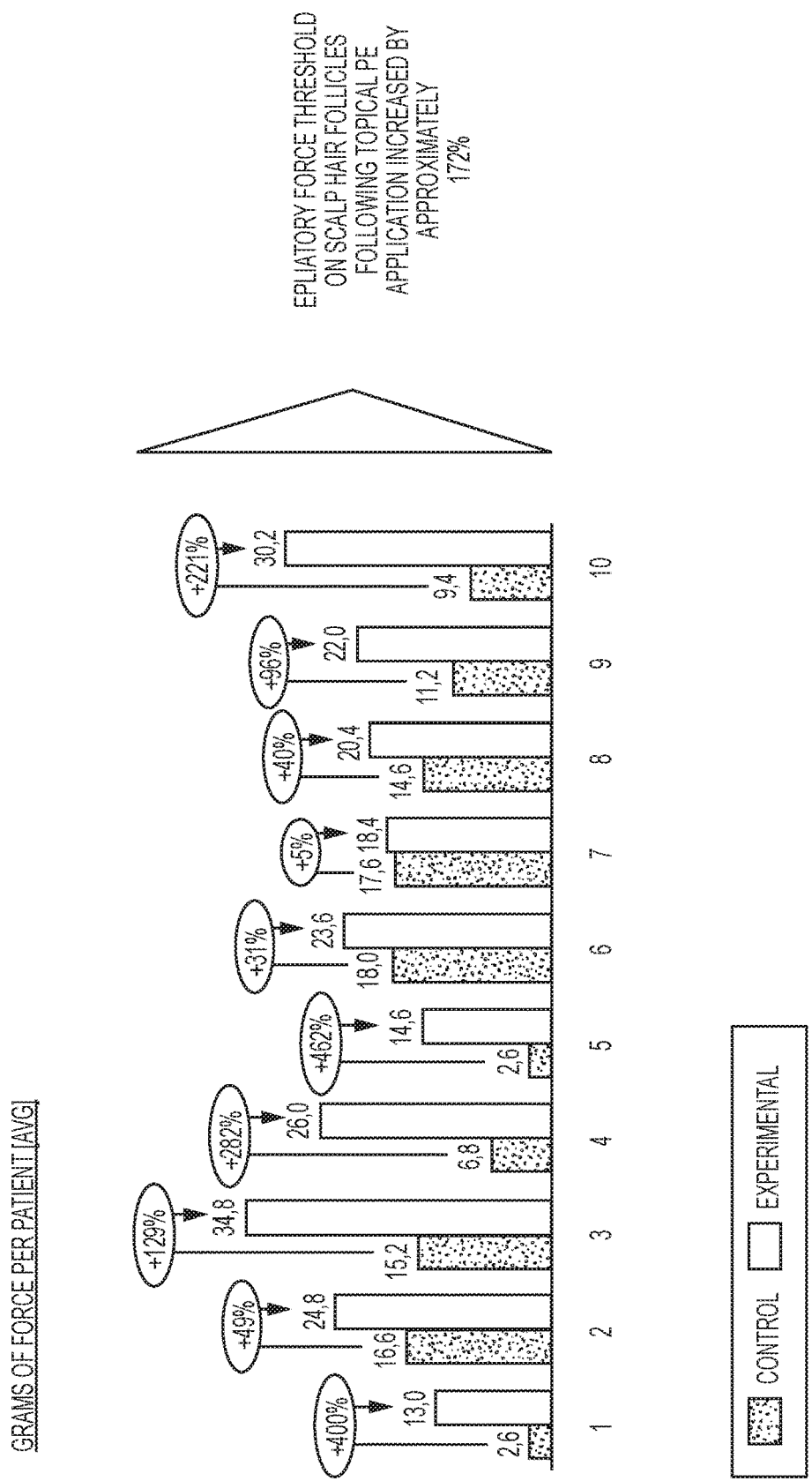

FIGS. 2 and 3 show that application of the 10% phenylephrine hydrochloride solution resulted in reduced hair shedding in 80% of the patients, as compared to the placebo solution containing the vehicle, with the average reduction being approximately 42%. FIGS. 4 and 5 show that the epiliatory force threshold for plucking hair follicles following topical 10% phenylephrine hydrochloride application increased by approximately 172%. Therefore, there is a significant reduction hair loss from mechanical pulling and increase in epilatory force after topical application of 10% phenylephrine hydrochloride. This novel study demonstrates the utility of α1-AR agonists in the treatment of traction alopecia and excessive hair loss resulting from mechanical cosmetic procedures.

Example 4: Synephrine HCl at 40%, 50% by Weight

A study was conducted to assess the dosage of topical synephrine solution required to elicit the pilomotor reflex of the hair arrecto-pili muscle. Five premenopausal subjects participated in the study. Two formulations were used: Formula A: 40% topical synephrine hydrochloride solution; Formula B: 50% topical synephrine hydrochloride solution in both of which solutions the synephrine was present in approximately a racemic mixture of (+/−) synephrine HCl.

The study was conducted over 2 days. On day 1, subjects were instructed to apply Formula A to their arm. On day 2, subjects were instructed to apply Formula B to their arm. 0.1 mL of each formula was applied using a metered dosage dispenser to each arm. Table 3 summarizes the finding from this study.

TABLE 3

Synephrine study

| Subject No. | Formula A | Formula B |
|---|---|---|
| 1 | NR | R |
| 2 | NR | R |
| 3 | NR | R |
| 4 | NR | NR |
| 5 | NR | R |

R = Response, i.e. goose bumps; NR = No response

The 50% topical Synephrine hydrochloride solution (Formula B) elicited a clinical response in 4 out of 5 subjects while Formula A failed to elicit a response.

Example 5: Phenylephrine

Female subjects, ages 18-40, were recruited to study the effect of topically applied phenylephrine, a selective α1-AR agonist, on epilation force and hair shedding during cosmetic procedures. In the blinded study, 80% of subjects demonstrated reduced shedding on days using phenylephrine compared to days using a placebo solution. The average reduction in hair loss was approximately 42%. In addition, the force threshold required for epilation increased by approximately 172% following topical phenylephrine application. To our knowledge this is the first study demonstrating the utility of α1-AR agonists in the treatment of traction alopecia and hair shedding during cosmetic procedures.

Methods:

Patients: Fifteen female subjects, ages 18-40, were included in the study. Subjects were recruited based on their frequent use of traumatic hair care practices, such as, tight braids, head scarves, ponytails, extensions, hair rollers, hair weaves and heated styling appliances such as blow dryers, flat irons, heat setters and curling irons. Subjects with uncontrolled hypertension, that were pregnant or breastfeeding, had been diagnosed with pattern hair loss or with other hair loss in conjunction with female pattern hair loss were excluded from the study. Prior to initiating the study, the efficacy of the 10% phenylephrine solution was tested by applying a small aliquot (50 µL) of the solution to the forearm of three subjects. Piloerection and blanching were visible after 30 minutes; the effect lasted for approximately 2-3 hours.

Hair Shedding: To measure hair loss during cosmetic procedures, a 4-day protocol was designed. On the first day patients were instructed to wash their hair and use styling products and procedures as they normally would. On the second day, patients were instructed not to wash their hair and to apply 0.5 mL of a placebo solution, containing a vehicle only, on the frontal area of the scalp in an 8×10 cm2 target area. Patients were instructed to wait 45 minutes, after which, they brushed their hair 20 times from the front of the scalp to the bottom of head using a new brush. After the procedure, the brushes were sealed in a plastic bag. On day three, patients were instructed to wash their hair and use styling products and procedures as they normally would. On the fourth day, patients repeated the procedures of day two; only they applied 0.5 mL of a 10% phenylephrine solution to the target area. After each clinical procedure, the investigator counted the hairs collected on each brush. A new brush was used for each procedure.

Epilation Force:

To evaluate the effect of a topically applied α1-AR agonist on the force required to pluck hairs from the scalp, a hand-held spring dynamometer, or "trichotillometer" was used (8). The trichotillometer records the maximum force threshold, in grams, required to pluck a single hair from the scalp; the performance and statistical variance of the instrument have been reported previously (8-10). Force measurements were performed using the trichotillometer on 10 subjects. The frontal area of scalp was divided into two 8×10 cm2 areas. On the right side 0.5 mL of a placebo vehicle was applied. On the left side, 0.5 mL a 10% phenylephrine solution was applied. After 45 minutes, ten hairs were plucked from each of the target areas with the trichotillometer.

Results:

After tabulating the data of 15 subjects studied in the hair shedding experiment (Table 1), we found a decrease in hair loss in 12 out of 15 patients (80%) in the target area following the application of 10% phenylephrine solution compared to hair loss in the targeted area following the application of a placebo solution. Reduction in hair loss varied from 9% to 100%, with an average reduction of 42%.

TABLE 1

Number of hairs removed with brush after the application of 10% phenylephrine (10% PE) or placebo.

| Patient # | Number of Hairs Removed with Brush | | |
|---|---|---|---|
| | Placebo | 10% PE | Reduction |
| 1 | 35 | 16 | 54% |
| 2 | 3 | 0 | 100% |
| 3 | 10 | 10 | 0% |
| 4 | 14 | 8 | 43% |
| 5 | 28 | 17 | 39% |
| 6 | 31 | 11 | 65% |
| 7 | 3 | 2 | 33% |
| 8 | 12 | 6 | 50% |
| 9 | 5 | 2 | 60% |
| 10 | 35 | 32 | 9% |
| 11 | 28 | 8 | 71% |
| 12 | 2 | 2 | 0% |
| 13 | 7 | 7 | 0% |
| 14 | 8 | 2 | 75% |
| 15 | 7 | 5 | 29% |
| | | AVERAGE | 42% |

Measurements of the epilation force threshold in 10 subjects showed similar improvements (Table 2). The epilation force threshold on scalp hair follicles increased 172% on average (range: 5% to 462%) following the application of a topical 10% phenylephrine solution.

TABLE 2

Grams of force required for epilation after the application of 10% phenylephrine (10% PE) or placebo. Each data point is the average of 10 plucked hairs [avg. (std.)].

| Patient # | Epilation Force (grams) | | |
|---|---|---|---|
| | Placebo | 10% PE | Increase |
| 1 | 2.6 (2.6) | 13.0 (6.6) | 400% |
| 2 | 16.6 (2.7) | 24.8 (2.9) | 49% |
| 3 | 15.2 (2.4) | 34.8 (2.9) | 129% |
| 4 | 6.8 (6.4) | 26.0 (7.9) | 282% |
| 5 | 2.6 (1.5) | 14.6 (4.8) | 462% |
| 6 | 18.0 (3.2) | 23.6 (11.1) | 31% |
| 7 | 17.6 (4.4) | 18.4 (2.3) | 5% |
| 8 | 14.6 (4.2) | 20.4 (4.6) | 40% |
| 9 | 11.2 (5.9) | 22.0 (5.5) | 96% |
| 10 | 9.4 (4.8) | 30.2 (8.3) | 221% |
| | | AVERAGE | 172% |

Discussion

At present, many people use various mechanical hair procedures, which result in increased traumatic force on hair follicles and result in traction alopecia. Each hair follicle in the human skin contains an arrector pili muscle, which expresses α1 adrenergic receptors (α1-AR). Stimulation of the arrector pili muscle with α1-AR agonist causes contraction of the muscle, which can provide a counterforce to resist epilation of hair follicles. In this experiment, we demonstrated that a 10% solution of phenylephrine, a selective α1 agonist, could induce piloerection on the scalp that reduced hair shedding and increased the threshold force for epilation. To our knowledge this is the first study elucidating the novel mechanism of α1-AR agonist induced piloerection for the treatment of traction alopecia and excessive hair shedding resulting from cosmetic procedures.

Example 6: Bitter Orange Extract

Highly purified (greater than 90%) natural bitter orange extract from *Citrus aurantium* was tested at 25% and 12.5% in a buffer solution at pH5.2 on the arms of four subjects to determine piloerection response. The 12.5% dosage failed to elicit a response. The 25% solution elicited a response. The response appeared after about 15-30 minutes. The piloerection lasted 3-4 hours.

REFERENCES

1. Ozçelik D. Extensive traction alopecia attributable to ponytail hairstyle and its treatment with hair transplantation. Aesthetic Plast Surg 2005: 29(4): 325-327.
2. Hjorth N. Traumatic marginal alopecia; a special type: alopecia *groenlandica*. Br J Dermatol 1957: 69(9): 319-322.
3. Khumalo N P, Jessop S, Gumedze F, Ehrlich R. Determinants of marginal traction alopecia in African girls and women. J Am Acad Dermatol 2008: 59(3): 432-438.
4. Hellmann K. The isolated pilomotor muscles as an in vitro preparation. J Physiol 1963: 169: 603-620.
5. Siepmann T, Gibbons C H, Illigens B M, Lafo J A, Brown C M, Freeman R. Quantitative pilomotor axon reflex test: a novel test of pilomotor function. Arch Neurol 2012: 69(11): 1488-1492.
6. Lewis T, Marvin H M. Observations upon a pilomotor reaction in response to faradism. J Physiol 1927: 64(1): 87-106.
7. Piascik M T, Perez D M. Alpha1-adrenergic receptors: new insights and directions. J Pharmacol Exp Ther 2001: 298(2): 403-410.
8. Wyness L A, McNeill G, Prescott G L. Trichotillometry: the reliability and practicality of hair pluckability as a method of nutritional assessment. Nutr J 2007: 6: 9.
9. Chase E S, Weinsier R L, Laven G T, Krumdieck C L. Trichotillometry: the quantitation of hair pluckability as a method of nutritional assessment. Am J Clin Nutr 1981: 34(10): 2280-2286.
10. Smelser D N, Smelser N B, Krumdieck C L, Schreeder M T, Laven G T. Field use of hair epilation force in nutrition status assessment. Am J Clin Nutr 1982: 35: 342-346.

The invention claimed is:

1. A method for treatment of traction alopecia comprising applying a composition comprising a pilomotor effective amount of synephrine, or a pharmaceutically acceptable salt or hydrate thereof, topically to a portion of skin on the head that includes at least one hair follicle to increase the epilatory force threshold of the at least one hair follicle.

2. The method of claim 1, wherein the at least one hair follicle is under tension.

3. The method of claim 1, wherein the portion of skin is at risk for developing traction alopecia.

4. The method of claim 1, wherein the synephrine is present in the composition in a concentration of 5% to 60% by weight.

5. The method of claim 1, wherein the composition comprises the 1-enantiomer of synephrine that is R-(−)-4-[1-hydroxy-2-(methylamino)ethyl]phenol and has less than 10% by weight of other enantiomers of synephrine.

6. The method of claim 5, wherein R-(−)-4-[1-hydroxy-2-(methylamino)ethyl]phenol is present in the composition at 20% to 40% by weight.

7. A method of reducing hair shedding during brushing, combing or showering, the method comprising applying a composition comprising a pilomotor effective amount of synephrine, or a pharmaceutically acceptable salt or hydrate thereof, topically to a portion of skin on the head that includes at least one hair follicle to increase the epilatory force threshold of the at least one hair follicle.

8. The method of claim 7, wherein the alpha 1 adrenergic receptor agonist is applied to the skin prior to the brushing or combing.

9. The method of claim 7, wherein the at least one hair follicle is under tension.

10. The method of claim 7, wherein the synephrine is present in the composition in a concentration of 5% to 60% by weight.

11. The method of claim 7, wherein the composition comprises the 1-enantiomer of synephrine that is R-(−)-4-[1-hydroxy-2-(methylamino)ethyl]phenol and has less than 10% by weight of other enantiomers of synephrine.

12. The method of claim 11, wherein R-(−)-4-[1-hydroxy-2-(methylamino)ethyl]phenol is present in the composition at 20% to 40% by weight.

13. A method for increasing epilatory force threshold of the hair, the method comprising applying a composition comprising a pilomotor effective amount of synephrine, or a pharmaceutically acceptable salt or hydrate thereof, topically to a portion of skin on the head of a person that includes at least one hair follicle to increase the epilatory force threshold of the at least one hair follicle.

14. The method of claim 13, wherein before, during or after the composition is applied, the person undergoes a cosmetic procedure to the hair selected from the group consisting of braiding, flat ironing, attaching a hair weave, attaching a hair extension, or tying the hair back in a ponytail.

15. The method of claim 13, wherein the synephrine is present in the composition in a concentration of 5% to 60% by weight.

16. The method of claim 13, wherein the composition comprises the 1-enantiomer of synephrine that is R-(−)-4-[1-hydroxy-2-(methylamino)ethyl]phenol and has less than 10% by weight of other enantiomers of synephrine.

17. The method of claim 16, wherein R-(−)-4-[1-hydroxy-2-(methylamino)ethyl]phenol is present in the composition at 20% to 40% by weight.

18. The method of claim 13, wherein the alpha 1 adrenergic receptor agonist is applied to the skin once daily.

19. The method of claim 13, wherein the composition of alpha 1 adrenergic receptor agonist is applied to the skin twice daily.

20. A method for treating traction alopecia comprising:
applying a composition comprising a pilomoter effective amount of synephrine, or a pharmaceutically acceptable salt or hydrate thereof, to the scalp to an area with a group of follicles that will experience a pulling force from a hair augmentation device to increase the epilatory force threshold of the group of follicles; and attaching the hair augmentation device to the group of follicles.

21. The method of claim 1, further comprising applying the composition to cause a hair of the at least one hair follicle to stand up and/or to cause puckering of the skin around a shaft of the hair.

22. The method of claim 7, further comprising applying the composition to cause puckering of the skin around a shaft of a hair of the at least one hair follicle.

23. The method of claim 13, further comprising applying the composition to cause puckering of the skin around a shaft of a hair of the at least one hair follicle.

24. The method of claim 20, further comprising applying the composition to cause puckering of the skin around a shaft of a hair of the at least one hair follicle.

\* \* \* \* \*